(12) United States Patent
Kogushi

(10) Patent No.: US 8,658,620 B2
(45) Date of Patent: Feb. 25, 2014

(54) PHARMACEUTICAL COMPOSITION, USE OF 2-IMINOPYRROLIDINE DERIVATIVE FOR PRODUCTION OF PHARMACEUTICAL COMPOSITION, AND KIT FOR TREATMENT OR AMELIORATION OF HEART DISEASES

(75) Inventor: Motoji Kogushi, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 169 days.

(21) Appl. No.: 12/812,058

(22) PCT Filed: Jan. 9, 2009

(86) PCT No.: PCT/JP2009/050184
§ 371 (c)(1),
(2), (4) Date: Jul. 8, 2010

(87) PCT Pub. No.: WO2009/088063
PCT Pub. Date: Jul. 16, 2009

(65) Prior Publication Data
US 2010/0286087 A1    Nov. 11, 2010

(30) Foreign Application Priority Data

Jan. 11, 2008  (JP) ................ 2008-004318

(51) Int. Cl.
*A61K 31/727* (2006.01)
*A01N 43/00* (2006.01)
*A61K 31/535* (2006.01)

(52) U.S. Cl.
USPC .................. 514/56; 514/161; 514/235.2

(58) Field of Classification Search
None
See application file for complete search history.

(56) References Cited

U.S. PATENT DOCUMENTS

| | | | |
|---|---|---|---|
| 7,244,730 B2 | 7/2007 | Suzuki et al. | |
| 2002/0013343 A1 | 1/2002 | Serebruany et al. | |
| 2005/0004204 A1 | 1/2005 | Suzuki et al. | |
| 2006/0058370 A1 | 3/2006 | Shimomura et al. | |
| 2010/0056519 A1 | 3/2010 | Serebruany et al. | |

FOREIGN PATENT DOCUMENTS

| | | |
|---|---|---|
| CN | 1503784 | 6/2004 |
| EP | 1391451 | 2/2004 |
| EP | 1 602 646 | 12/2005 |
| EP | 1614680 | 1/2006 |
| EP | 1721610 A1 | 11/2006 |
| EP | 1813282 A1 | 8/2007 |
| WO | 02/085855 | 10/2002 |
| WO | 2004/078721 | 9/2004 |
| WO | 2007/075964 | 7/2007 |
| WO | WO 2007/075964 | * 7/2007 |
| WO | WO 2007/117621 | * 10/2007 ......... A61K 31/4525 |
| WO | WO2007117621 A1 | 10/2007 |

OTHER PUBLICATIONS

Watson et al (BMJ 325:1348-1351, 2002).*
Chackalamannil et al, Expert Opin Ther Patents 16(4):493-505, 2006.*
Patrono et al, NEJM 353:2373-2383, 2005.*
Brouwer et al., "Adjunctive Treatment in Patients Treated with Thrombolytic Therapy", Heart, 90(5):581-588 (2004).
Chackalamannil, S., "Thrombin Receptor (Protease Activated Receptor-1) Antagonists as Potent Antithrombotic Agents with Strong Antiplatelet Effects", J. of Med. Chem., 49(18):5389-5403 (2006).
Joseph et al., "New antiplatelet drug", Blood Reviews, 11:178-190 (1997).
R&D Meeting, Major Project Status and Future Plan, Eisai Co., Ltd., Aug. 30, 2005, 48 pages.
EP Search Report issued for EP Patent Application No. 09701323.9 dated Feb. 29, 2012.
Office Action for CN Patent Application No. 200980101834.9 issued on Nov. 9, 2011 with English translation.
Response to CN Office Action for CN Application No. 200980101834.9 filed on Mar. 13, 2012 with English translation.
Office Action issued for IL Patent Application No. 206464 on Aug. 25, 2011 with English translation.
Response to the Office Action for IL Patent Application No. 206464 filed on Nov. 13, 2011 with English translation.
Bode et al., "Activation and adherence of the lyophlized human platelets on canine vessel strips in the Baumgartner perfusion chamber", J. Lab. Clin. Med, 133 (2); 200-11, (Feb. 1999).
Calvete J.J., On the Structure and Function of Platelet Integrin $\alpha11b\beta3$, the Fibrinogen Receptor (43863A), Proc, Soc, Exp. BioI. Med. 208 (4); 346--60 (1995).
Shattil S.l., "Signaling Through Platelet Integrin $\alpha11b\beta3$: Inside-out, Outside-in, and Sideways", Thrombosis, Haemostasis, 82 (2): 318-25 (1999).
Charo et al., "The Vitronectin Receptor alpha v beta 3 Binds Fibronectin and Acts in Concert with alpha 5 beta 1 in Promoting Cellular Attachment and Spreading on Fibronectin", The Journal of Cell Biology, 111(6): 2795-2800 (1990).
Silverstein et aI., "Sense and Antisense cDNA Transfection of CD36 (Glycoprotein IV) in Melanoma Cells", .Journal of Biological Chemistry. 267(23):16607-16612, (1992).
Konstantopoulos et al., "Venous Levels of Shear Support Neutrophil-Platelet Adhesion and Neutrophil Aggregation in blood via P-Selectin and beta 2-Integrin", Circulation. 98: 873-882, (1998).
Wang et al., "VK0RC1 Haplotypes Are Associated With Arterial Vascular Diseases (Stroke, Coronary Heart Disease, and Aortic Dissection)" Circulation. 113: 1615-1621 (2006).

(Continued)

Primary Examiner — Craig Ricci
(74) Attorney, Agent, or Firm — Fish & Richardson P.C.

(57) ABSTRACT

One embodiment of the present invention is a pharmaceutical composition comprising at least one specific 2-iminopyrrolidine derivative and at least one other compound (B). Another embodiment of the present invention is a pharmaceutical composition comprising at least one specific 2-iminopyrrolidine derivative, which is to be used in combination with at least one other compound (B). According to the present invention, there are provided pharmaceutical compositions capable of treating or ameliorating diseases, such as heart diseases, effectively.

3 Claims, 1 Drawing Sheet

(56) References Cited

OTHER PUBLICATIONS

International Search Report issued for International application No. PCT/JP2009/050184, dated Mar. 17, 2009 with English translation.
International Preliminary Report on Patentability (Chapter I) for international application No. PCT/JP2009/050184, dated Jul. 13, 2010 with English translation.
International Preliminary Report on Patentability for international application No. PCT/JP2009/050184, dated Aug. 10, 2010 with English translation.
Communication issued for EP patent application No. 09701323.9, dated Aug. 18, 2010.
Amendment filed for EP patent application No. 09701323.9 filed on Sep. 17, 2010.
Form 3 for IN patent application No. 4856/CEHNP/2010, filed around Jan. 13, 2011.
Response to the Office Action for U.S. Appl. No. 12/502,899, filed Feb. 18, 2011.
Request for Continued Examination for U.S. Appl. No. 12/502,899, filed Oct. 5, 2011.
Final Office Action for U.S. Appl. No. 12/502,899 dated Feb. 15, 2012.
Office Action issued for the corresponding Israeli patent application No. 206464 on Feb. 23, 2012 with English translation.
Communication issued for EP patent application No. 09701323.9 dated Mar. 19, 2012.
Response to the Office Action for EP patent application No. 09701323.9 dated Sep. 28, 2012.
Response to the Office Action for Israeli patent application No. 206464, filed Jun. 11, 2012 with English translation.
Request for Continued Examination for U.S. Appl. No. 12/502,899, filed Jun. 13, 2012.
Office Action for U.S. Appl. No. 12/502,899 dated Jan. 18, 2011.
Office Action for Australian Patent Application No. 2009203368 dated Jun. 7, 2013.
Office Action for Mexican Patent Application No. MX/a/2010/007527 dated Jul. 22, 2013.
Office Action corresponding Israeli Patent Application No. 206464 dated Apr. 25, 2013.
Chen et al., "Analytical Tools and Approaches for Metabolite Identification in Early Drug Discovery", Pharma. Res. 24(2):248-257 (2007).
Morissette et al., "High-throughput crystallization: polymorphs, salts, co-crystals and solvates of pharmaceutical solids", Adv. Drug Delivery Rev. 56:275-300, 2004.
Tschoepe et al., "Platelet Membrane Activation Markers Are Predictive for Increased Risk of Acute Ischemic Events After PTCA", Circulation, 88:37-42 (1993).
Vippagunta et al., "Crystalline Solids", Adv. Drug Delivery Rev. 45:3-26 (2001).
U.S. Office Action for U.S. Appl. No. 12/502,899 dated Apr. 7, 2011.
Office Action for corresponding Japanese Patent Application No. JP2009-548960 dated Sep. 24, 2013.

* cited by examiner

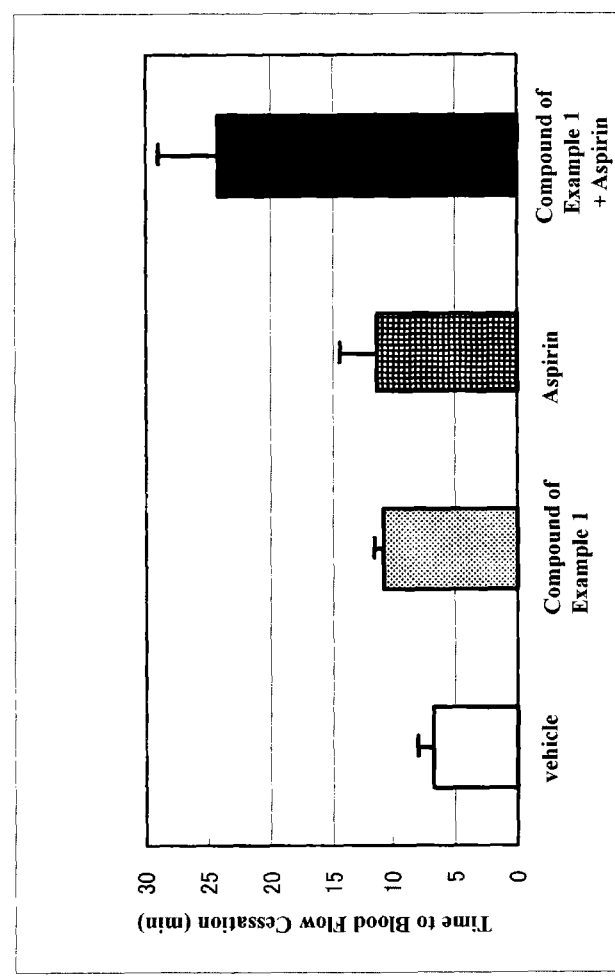

PHARMACEUTICAL COMPOSITION, USE OF 2-IMINOPYRROLIDINE DERIVATIVE FOR PRODUCTION OF PHARMACEUTICAL COMPOSITION, AND KIT FOR TREATMENT OR AMELIORATION OF HEART DISEASES

TECHNICAL FIELD

The present invention relates to a pharmaceutical composition, use of 2-imminopyrrolidine derivative for manufacturing a pharmaceutical composition, a kit for treating or ameliorating heart diseases, etc.

BACKGROUND ART

Heart diseases include acute coronary syndrome, atherothrombosis, restenosis, hypertension, stable angina, arrhythmia, cardiac failure, ST-segment elevation myocardial infarction, and the like. As a target substance in the treatment of these heart diseases, thrombin is contemplated which is one of blood coagulation factors. Receptors for GP (glycoprotein) IIb/IIIa (platelet membrane glycoproteins) can also be targets for treating heart diseases. Further, it is known that thrombin receptors are present in cells such as platelets, vascular smooth muscle cells, endothelial cells and fibroblast cells. Thrombin receptors can also be targets for treating heart diseases.

DISCLOSURE OF THE INVENTION

Problem for Solution by the Invention

Under circumstances, pharmaceutical compositions capable of effectively treating or ameliorating heart diseases or the like have been demanded.

Means to Solve the Problem

As a result of intensive and extensive researches toward solution of the above problem, the present inventors have found that it is possible to treat or ameliorate heart diseases or the like effectively by administering at least one specific 2-iminopyrrolidine derivative in combination with at least one other compound (B). Thus, the present invention has been achieved.

The present invention may be summarized as follows.
(1) A pharmaceutical composition comprising at least one compound selected from the group consisting of the formulas (I) to (VII) described below or a pharmacologically acceptable salt thereof and at least one other compound (B) selected from the group B described below.

According to one embodiment of the present invention, the composition is a pharmaceutical composition for treating or ameliorating heart diseases.
(2) Use of at least one compound selected from the group consisting of the formulas (I) to (VII) described below or a pharmacologically acceptable salt thereof for manufacturing a pharmaceutical composition for treating or ameliorating heart diseases, wherein the pharmaceutical composition is to be used in combination with at least one other compound (B) selected from the group B described below.
(3) A kit for treating or ameliorating heart diseases, which contains a pharmaceutical composition comprising at least one compound selected from the group consisting of the formulas (I) to (VII) described below or a pharmacologically acceptable salt thereof and a pharmaceutical composition comprising at least one other compound (B) selected from the group B described below.
(4) A method of treating or ameliorating heart diseases, comprising administering to a patient simultaneously or separately an effective amount of at least one compound selected from the group consisting of the formulas (I) to (VII) described below or a pharmacologically acceptable salt thereof and an effective amount of at least one other compound (B) selected from the group B described below.

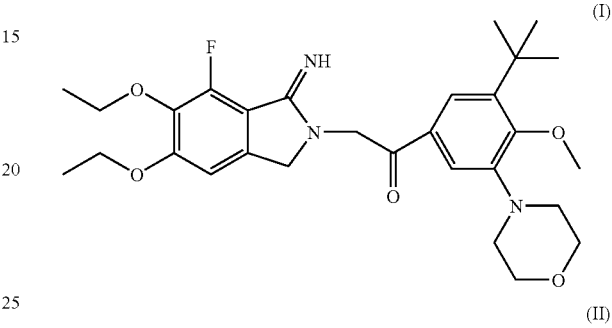

(I)

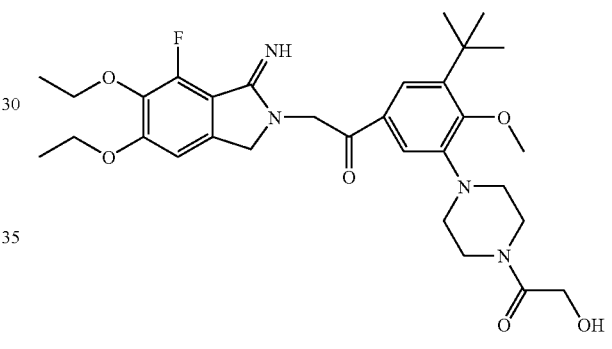

(II)

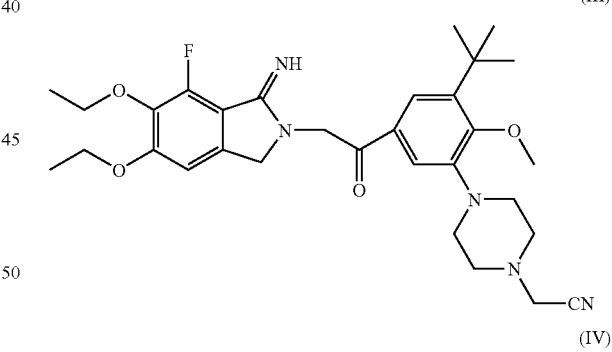

(III)

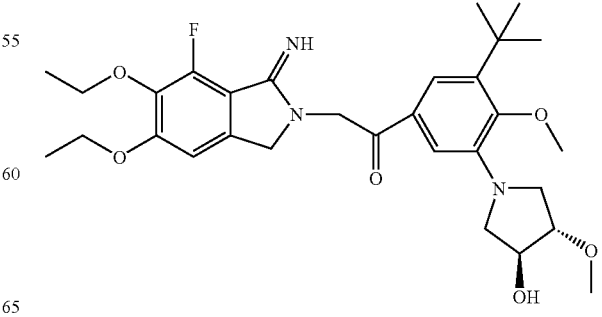

(IV)

-continued

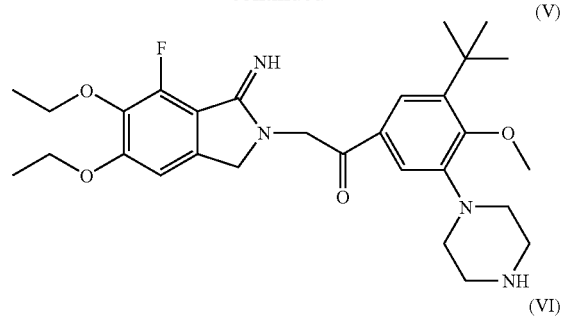

(V)

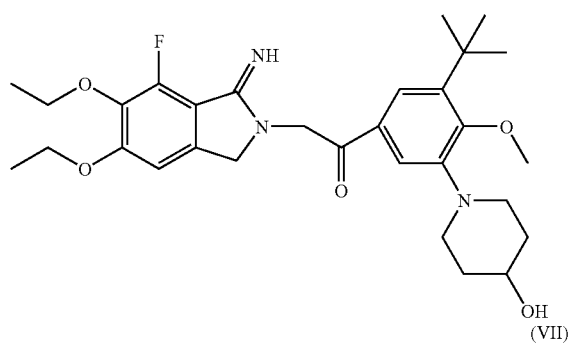

(VI)

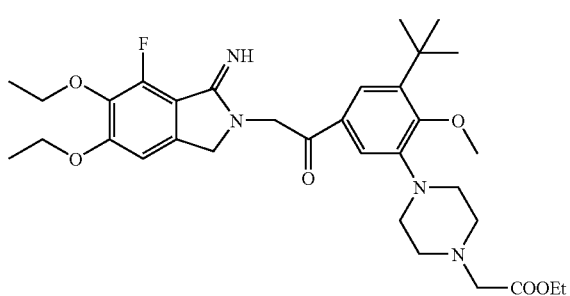

(VII)

Group B cyclooxygenase inhibitor, thromboxane A2 biosynthesis inhibitor, thromboxane receptor antagonist, adenosine diphosphate receptor antagonist, GPIIb/IIIa antagonist, PGE1 or PGI2 derivative, platelet aggregation inhibitor, serotonin receptor antagonist, thrombin inhibitor, heparin, low molecular weight heparin, Xa inhibitor, VIIa inhibitor, K$^+$ channel inhibitor, vitamin K antagonist, angiotensin antagonist, angiotensin-converting enzyme inhibitor, endothelin antagonist, phosphodiesterase inhibitor, calcium antagonist, β blocker, nitrite, thrombolytic agent, HMG-CoA reductase inhibitor, fibrate drug, nicotinate drug, bile acid adsorbent, cholesterol absorption inhibitor, PPAR-γ agonist, PPAR-α agonist, PPAR-β agonist, neutral endopeptidase inhibitor and diuretic agent.

In the present invention, examples of the at least one compound selected from the group consisting of the formulas (I) to (VII) or the pharmacologically acceptable salt thereof include a hydrobromide of the compound represented by the formula (I).

In one embodiment of the present invention, as the heart disease, at least one disease selected from the group consisting of acute coronary syndrome, atherothrombosis, restenosis, hypertension, stable angina, arrhythmia, cardiac failure, ST-segment elevation myocardial infarction and cerebral infarction may be given.

In the present invention, examples of the compound (B) include aspirin which is a cyclooxygenase inhibitor or clopidogrel which is an adenosine diphosphate receptor antagonist.

Effect of the Invention

The present invention provides pharmaceutical compositions capable of treating or ameliorating diseases effectively. According to preferred embodiments of the present invention, it is possible to treat or ameliorate heart diseases effectively.

BRIEF DESCRIPTION OF THE DRAWINGS

FIG. 1 is a graph showing the antithrombotic effects of the compound of Example 1, aspirin, and combined administration of both compounds in a guinea pig photosensitization-induced thrombus model.

BEST MODE FOR CARRYING OUT THE INVENTION

Hereinbelow, the present invention will be described in more detail. The embodiments described below are provided only for the purpose of illustration of the present invention, and are not intended to limit the present invention to those embodiments. The present invention may be practiced in various forms without departure from the scope of the invention.

All publications and patent documents, such as unexamined patent publications and patents, cited herein are incorporated herein by reference in their entirety. The present specification encompasses the contents disclosed in the specifications and the drawings of Japanese Patent Application No. 2008-4318 and U.S. Provisional Patent Application No. 61/020,426 based on which the present patent application claims priority.

According to one embodiment of the present invention, there is provided a pharmaceutical composition comprising at least one 2-iminopyrrolidine derivative and at least one other compound (B). According to another embodiment of the present invention, there is provided a pharmaceutical composition comprising at least one 2-iminopyrrolidine derivative, which is to be used in combination with at least one other compound (B). Preferably, these pharmaceutical compositions are for treating or ameliorating heart diseases.

(1) 2-Iminopyrrolidine Derivatives

The 2-iminopyrrolidine derivative contained in the pharmaceutical composition of the present invention is at least one (e.g., one) compound selected from the group consisting of the following formulas (I) to (VII) or a pharmacologically acceptable salt thereof.

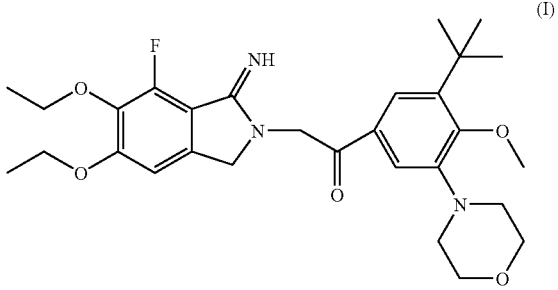

(I)

(II)

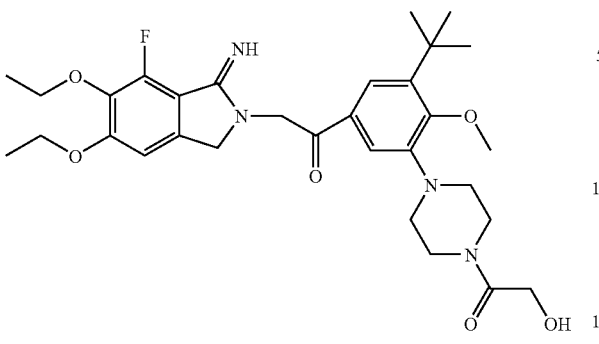

(III)

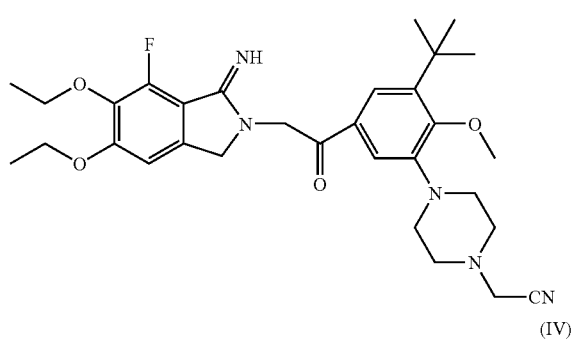

(IV)

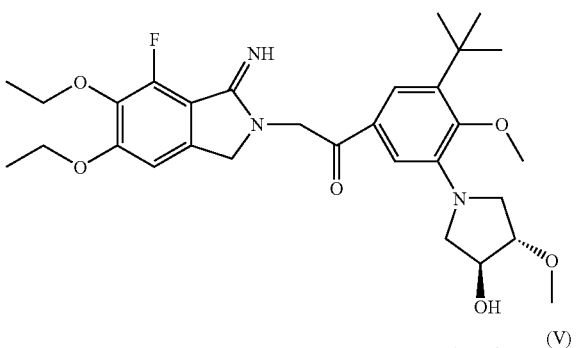

(V)

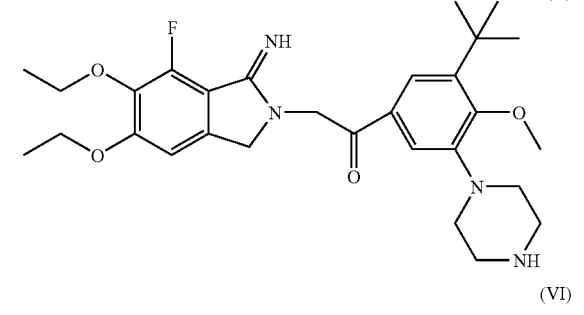

(VI)

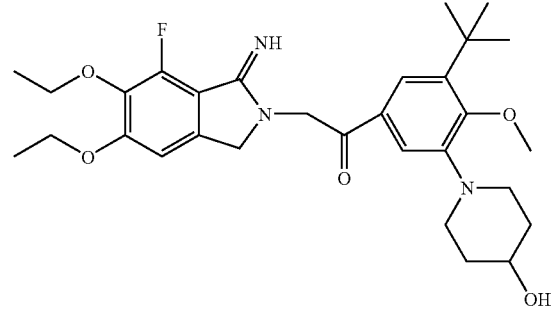

(VII)

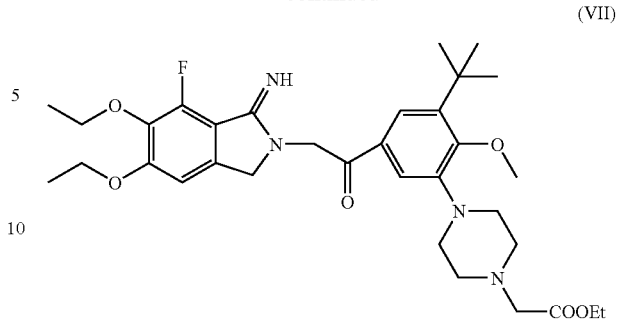

The 2-iminopyrrolidine derivative used in the present invention is preferably a compound represented by the formula (I) or a pharmacologically acceptable salt thereof, more preferably a hydrobromide of a compound represented by the formula (I).

In the present invention, the pharmacologically acceptable salt is not particularly limited as long as it has a therapeutic effect or ameliorating effect on heart diseases and is pharmacologically acceptable. Specific examples of pharmacologically acceptable salts include hydrogen halide acid salts (for example, hydrofluoride, hydrochloride, hydrobromide and hydroiodide), inorganic acid salts (for example, sulfate, nitrate, perchlorate, phosphate, carbonate and bicarbonate), organic carboxylates (for example, acetate, oxalate, maleate, tartarate, fumarate and citrate), organosulfonates (for example, methanesulfonate, trifluoromethanesulfonate, ethanesulfonate, benzenesulfonate, toluenesulfonate and camphorsulfonate), amino acid salts (for example, aspartate and glutamate), quaternary amine salts, alkali metal salts (for example, sodium salts and potassium salts) and alkaline earth metal salts (for example, magnesium salts and calcium salts).

When the 2-iminopyrrolidine derivative has geometrical isomers and optical isomers such as diastereomer, these isomers may also be included in the compound of the present invention or the pharmacologically acceptable salt thereof as long as the isomers have a therapeutic or ameliorating effect on heart diseases.

Further, the 2-iminopyrrolidine derivative may be either an anhydride or a solvate such as hydrate. Although the solvate may be either hydrate or non-hydrate, hydrate is preferable. As the solvent, water, alcohol (for example, methanol, ethanol and n-propanol), dimethylformamide or the like may be used. These solvates may also be included in the compound of the present invention or the pharmacologically acceptable salt thereof as long as the solvates have a therapeutic or ameliorating effect on heart diseases.

The 2-iminopyrrolidine derivative contained in the pharmaceutical composition of the present invention (preferably, a hydrobromide of a compound represented by the formula (I) above) is an antagonist for protease-activated receptor (PAR1) which is one of thrombin receptors. Since PAR1 antagonist has at least one activity selected from the group consisting of antithrombotic activity, anti-platelet aggregation activity, anti-atherosclerotic activity and anti-restenotic activity, it is possible to use the 2-iminopyrrolidine derivative (preferably, a hydrobromide of a compound represented by the formula (I) above) to treat or ameliorate at least one disease selected from the group consisting of acute coronary syndrome (for example, ST-segment non-elevation myocardial infarction and unstable angina), atherothrombosis (for example, peripheral arterial occlusive disease), restenosis, hypertension, stable angina, exercise-induced angina, angina at rest, arrhythmia, cardiac failure, ST-segment elevation myocardial infarction, thrombotic stroke, thromboembolic stroke, venous thromboembolism, deep venous thrombosis, pulmonary embolism, atherosclerosis, peripheral vascular disease, inflammatory disease, cerebral ischemia, cerebral infarction, other occlusive vascular diseases, disseminated intravascular coagulation, rheumatism, asthma, glomerulonephritis, osteoporosis and neurological disorders.

(2) Method of Preparation of 2-Iminopyrrolidine Derivatives

The 2-iminopyrrolidine derivative used in the present invention, i.e., at least one (e.g., one) compound selected from the group consisting of the formulas (I) to (VII) or a pharmacologically acceptable salt thereof, may be prepared by methods described, for example, in WO 02/085855 and WO 04/078721. More specifically, these compounds or pharmacologically acceptable salts thereof may be prepared by the methods described from page 40, line 24 to page 139, line 15; from page 170, line 6 to page 177, line 12 (Example 7); from page 177, line 13 to page 183, line 1 (Example 8); from page 190, line 21 to page 193, line 2 (Example 11); from page 200, line 11 to page 203, line 1 (Example 14); from page 203, line 2 to page 205, line 17 (Example 15); from page 316, line 7 to page 317, line 3 (Example 112); and from page 325, line 3 to line 13 of the same page (Example 125) of WO 02/085855; or by methods pursuant thereto. Alternatively, these compounds or pharmacologically acceptable salts thereof may be prepared by the method described throughout the entire specification of WO 04/078721 or a method pursuant thereto.

In Example 1 described later, a method of preparation of the 2-iminopyrrolidine derivative is illustrated taking hydrobromide and hydrochloride of the compound represented by the formula (I) as examples. Those compounds represented by the formulas (II) to (VII) or pharmacologically acceptable salts thereof may be prepared, for example, by a method pursuant to the method of Example 1.

(3) Pharmaceutical Compositions

The pharmaceutical composition of the present invention comprises at least one (for example, one) 2-iminopyrrolidine derivative. In the present invention, the specific 2-iminopyrrolidine derivative is at least one compound selected from the group consisting of the formulas (I) to (VII) or a pharmacologically acceptable salt thereof.

The pharmaceutical composition of the present invention is used for treating or ameliorating heart diseases. The term "treatment" or "amelioration" generally means obtaining a desired pharmacological and/or physiological effect. The effect may be prophylactic in terms of completely or partially preventing a disease and/or a symptom and may be therapeutic in terms of partially or completely curing a disease and/or an adverse effect attributed to the disease. The term "treatment" or "amelioration" used herein covers any treatment or amelioration of a disease in a mammal patient, preferably a human, and also includes the above-described general meaning of treatment. The "treatment or amelioration" includes at least one of the following (a) to (c):

(a) preventing a disease or a symptom from occurring in a patient who may be predisposed to the disease but has not yet been diagnosed as having it;

(b) inhibiting a disease symptom, i.e. preventing or delaying its progress; or (c) relieving a disease symptom, i.e. causing regression or elimination of the disease or symptom, or causing reversal of the progress of the disease.

In the present invention, the 2-iminopyrrolidine derivative is at least one compound selected from the group consisting of the formulas (I) to (VII) or a pharmacologically acceptable salt thereof, preferably a compound represented by the formula (I) or a pharmacologically acceptable salt thereof more preferably a hydrobromide of a compound represented by the formula (I).

In the pharmaceutical composition of the present invention, at least one compound selected from the group consisting of the formulas (I) to (VII) or a pharmacologically acceptable salt thereof may be used as it is. Alternatively, the compound or the salt thereof may be formulated into a preparation with known pharmacologically acceptable carriers or the like. Examples of such pharmacologically acceptable carriers include fillers, binders, disintegrants, lubricants, coloring agents, flavoring agents, stabilizers, emulsifiers, absorbefacients, surfactants, pH adjusting agents, antiseptics, antioxidants, etc.

The administration route of the pharmaceutical composition of the present invention is not particularly limited. The pharmaceutical composition may be administered either orally or parenterally depending on the dosage form described above. Forms of parenteral administration include intravenous injection, intravenous infusion, subcutaneous injection, transdermal injection, intraperitoneal injection and so on. Examples of formulated preparations include tablets, powders, subtle granules, granules, capsules, syrups, etc. for oral administration; and suppositories, injections, ointments, cataplasms etc. for parenteral administration.

Oral preparations for oral administration may be produced by adding to the active ingredients fillers, and if necessary, binders, disintegrants, lubricants, coloring agents, flavoring agents, etc. and formulating the resultant mixture according to conventional procedures into tablets, coated tablets, granules, subtle granules, powders, capsules or the like.

Examples of the filler include lactose, corn starch, white sugar, glucose, sorbitol, crystalline cellulose, silicon dioxide, etc. Examples of the binder include polyvinyl alcohol, ethylcellulose, methylcellulose, gum arabic, hydroxypropyl cellulose, hydroxypropyl methylcellulose, etc. Examples of the lubricant include magnesium stearate, talc, silica, etc. The coloring agent may be any coloring agent which is approved to be added to pharmaceutical preparations. Examples of the flavoring agent include cocoa powder, menthol, aromatic powder, peppermint oil, camphol, cinnamon powder, etc. Resultant tablets and granules may be appropriately coated with, for example, sugar or gelatin according to necessity.

In the present invention, injection preparations may be prepared by adding to the base component non-aqueous diluents (for example, glycols such as propylene glycol and polyethylene glycol; vegetable oils such as olive oil; and alcohols such as ethanol), suspending agents, dissolution aids, stabilizers, isotonizing agents, preservatives, pH adjusting agents, buffers and so forth. Sterilization of injection preparations may be performed, for example, by filter sterilization or by adding a disinfectant. Injection preparations may be formulated into an extemporaneous preparation that is prepared at the time of use. Briefly, an aseptic solid composition may be prepared by lyophilization or the like, and dissolved in an aseptic distilled water for injection or other solvent before use. When the pharmaceutical composition of the present invention is administered transdermally in the form of patch, it is preferable to select the so-called free-form that does not form a salt. Injection preparations may be produced as intravenous infusion preparations or intravesous, subcutaneous or intramuscular injection preparations according to conventional procedures.

Examples of the suspending agent include methylcellulose, polysolvate 80, hydroxyethyl cellulose, gum arabic, powdered tragacanth, sodium carboxymethylcellulose, polyoxyethylene sorbitan monolaurate, etc.

Examples of the dissolution aid include polyoxyethylene hydrogenated castor oil, polysolvate 80, nicotinamide, polyoxyethylene sorbitan monolaurate, macrogol, fatty acid ethyl ester from castor oil, etc.

Examples of the stabilizer include sodium sulfite, sodium metasulfite, etc. Examples of the preservative include methyl parahydroxybenzoate, ethyl parahydroxybenzoate, sorbic acid, phenol, cresol, chlorocresol, etc.

Although the effective doses of the compounds represented by the formulas (I) to (VII) or pharmacologically acceptable salts thereof in oral administration vary depending on the severity of symptom, the age, sex, body weight and sensitivity difference of the patient, the mode, time, interval and duration of administration, the nature, formulation and type of the preparation, the type of the active ingredient, etc., those skilled in the art could appropriately select the effective dose. For example, the compound or a pharmacologically acceptable salt thereof may be administered to an adult (body weight: 60 kg) at a daily dose of 0.001 mg to 10,000 mg, preferably 0.1 mg to 1000 mg, and more preferably 1 mg to 1000 mg for oral administration.

Although the effective doses of the compounds represented by the formulas (I) to (VII) or pharmacologically acceptable salts thereof in parenteral administration (e.g., injection) vary depending on the severity of symptom, the age, sex, body weight and sensitivity difference of the patient, the mode, time, interval and duration of administration, the nature, formulation and type of the preparation, the type of the active ingredient, etc., those skilled in the art could appropriately select the effective dose and appropriately administer to those patients in need of treatment by dissolving or suspending in a pharmacologically acceptable carrier (such as physiological saline or commercially available distilled water for injection) to give an appropriate concentration. For example, in the case of an injection preparation, the compound or a pharmacologically acceptable salt thereof may be administered to an adult (body weight: 60 kg) at a daily dose of 0.001 mg to 10,000 mg, preferably 0.01 mg to 1000 mg, and more preferably 0.1 mg to 1000 mg.

(4) Combined Use of 2-Iminopyrrolidine Derivative and Other Compound (B)

In the present invention, in order to treat or ameliorate diseases such as heart disease, at least one other compound (B) is used in combination with at least one (for example, one) of the 2-iminopyrrolidine derivatives described above. The "combined use" refers to a combination of at least one other compound (B) and the above-described 2-iminopyrrolidine derivative and encompasses both of the following modes of administration: (i) the compound (B) and the 2-iminopyrrolidine derivative are administered simultaneously or consecutively and (ii) the compound (B) and the 2-iminopyrrolidine derivative are administered in the form of a mixture (combined preparation). Briefly, "combined use" not only means that the compound (B) and the 2-iminopyrrolidine derivative are administered at exactly the same time. As long as an administration schedule includes a mode of administration in which the compound (B) and the 2-iminopyrroline derivative are administered, such a mode of administration means "combined use".

For the purpose of combined use, the other compound (B) may be contained in a pharmaceutical composition comprising the 2-iminopyrrolidine derivative. Alternatively, the other compound (B) may be contained in a pharmaceutical composition which is different from a pharmaceutical composition comprising the 2-iminopyrrolidine derivative.

The other compound (B) is preferably a drug having at least one effect selected from the group consisting of antithrombotic effect, anti-platelet aggregation effect, anti-atherosclerotic effect, anti-restenotic effect and anticoagulant effect.

The other compound (B) is preferably at least one therapeutic selected from the group B described below.

(Group B)

cyclooxygenase inhibitor, thromboxane A2 biosynthesis inhibitor, thromboxane receptor antagonist, adenosine diphosphate (ADP) receptor antagonist, GPIIb/IIIa antagonist, PGE1 or PGI2 derivative, platelet aggregation inhibitor, serotonin receptor antagonist, thrombin inhibitor, heparin, low molecular weight heparin, Xa inhibitor, VIIa inhibitor, $K^+$ channel inhibitor, vitamin K antagonist, angiotensin antagonist, angiotensin-converting enzyme (ACE) inhibitor, endothelin antagonist, phosphodiesterase inhibitor, calcium antagonist, β blocker, nitrite, thrombolytic agent, HMG-CoA reductase inhibitor, fibrate drug, nicotinate drug, bile acid adsorbent, cholesterol absorption inhibitor, PPAR-γ agonist, PPAR-α agonist, PPAR-β agonist, neutral endopeptidase inhibitor and diuretic agent.

Specific examples of the above-listed compounds of group B include the following compounds.

(1) Cyclooxygenase inhibitor: aspirin, meloxicam, rofecoxib, celecoxib, etc.

(2) Thromboxane A2 biosynthesis inhibitor: ozagrel, etc.

(3) Thromboxane receptor antagonist: seratrodast, picotamide, ramatroban, etc.

(4) Adenosine diphosphate receptor antagonist: clopidogrel, prasugrel, AZD-6140, cangrelor, ticlopidine, etc.

(5) GPIIb/IIIa antagonist: abciximab, eptifibatide, tirofiban, etc.

(6) PGE1 or PGI2 derivative: limaprost, beraprost, etc.

(7) Platelet aggregation inhibitor: cilostazol, dipyridamole, etc.

(8) Serotonin receptor antagonist: sarpogrelate hydrochloride, etc.

(9) Thrombin inhibitor: argatroban, bivalirudin, dabigatran, etc.

(10) Heparin and low molecular weight heparin: unfractionated heparin, enoxaparin, etc.

(11) Xa inhibitor: fondaparinux, rivaroxaban, apixaban, etc.

(12) VIIa inhibitor: rNAPc2, PCI-27483, etc.

(13) $K^+$ channel inhibitor: bepridil, sotalol, etc.

(14) Vitamin K antagonist: warfarin, etc.

(15) Angiotensin antagonist: valsartan, telmisartan, candesartan, irbesartan, isosartan, eprosartan, etc.

(16) Angiotensin-converting enzyme inhibitor: captopril, enalapril, enaliprilat, spirapril, quinapril, perindopril, ramipril, fosinopril, trandolapril, lisinopril, moexipril, benazepril, etc.

(17) Endothelin antagonist: tezosentan, etc.

(18) Phosphodiesterase inhibitor: milrinone, enoximone, etc.

(19) Calcium antagonist: amrodipine, etc.

(20) β blocker: atenolol, propranolol, etc.

(21) Nitrite: nitroglycerin, isosorbide dinitrate, etc.

(22) Thrombolytic agent: urokinase, streptokinase, tissue plasminogen activator, etc.

(23) HMG-CoA reductase inhibitor: atorvastatin, fluvastatin, pravastatin, etc.

(24) Fibrate drug: gemfibrozil, fenofibrate, bezafibrate, etc.

(25) Nicotinate drug: niacin, etc.

(26) Bile acid adsorbent: cholestyramine, cholestipol, etc.

(27) Cholesterol absorption inhibitor: ezetimibe, etc.

(28) PPAR-γ agonist: pioglitazone, etc.

(29) PPAR-α agonist: LY518674, WY14643, etc.

(30) PPARβ/δ agonist: GW501516, L165041, etc.

(31) Neutral endopeptidase inhibitor: candoxatril, ecadotril, etc.

(32) Diuretic agent: chlorothiazide, hydrochlorothiazide, ethacrynic acid, furosemide, amiloride, etc.

The other compound (B) used in combination with the above-described 2-iminopyrrolidine derivative is preferably a cyclooxygenase inhibitor, thromboxane A2 biosynthesis inhibitor, thromboxane receptor antagonist, adenosine diphosphate receptor (ADP) antagonist, GPIIb/IIIa antagonist, PGE1 or PGI2 derivative, phosphodiesterase inhibitor or platelet aggregation inhibitor. More preferably, the other compound (B) is aspirin or clopidogrel.

The other compound (B) may be administered either orally or parenterally, and may be formulated into various preparations in the same manner as described in the formulation of pharmaceutical compositions.

The effective dose of the other compound (B) is not particularly limited as long as it exhibits efficacy. Preferably, the effective dose is the dose level at which the compound (B) is used as a single drug, or below that level. Specifically, the compound (B) may be administered to an adult (body weight: 60 kg) at a daily dose of 0.015 mg to 4,000 mg, preferably 50 mg to 400 mg, for example. The compound (B) may be administered, for example, about 0.0001 to 100 fold (weight ratio), preferably about 0.1 to 10 fold (weight ratio), relative to the 2-iminopyrrolidine derivative.

More specifically, when the 2-iminopyrrolidine derivative is combined with aspirin, doses of these compounds are not particularly limited. For example, the 2-iminopyrrolidine derivative may be administered to an adult (body weight: 60 kg) at a daily dose of 1 mg to 1,000 mg, preferably 10 mg to 600 mg, more preferably 50 mg to 400 mg; and aspirin may be administered to an adult (body weight: 60 kg) at a daily dose of 10 mg to 1,000 mg, preferably 50 mg to 600 mg, more preferably 80 mg to 350 mg. Further, the ratio of the dose of aspirin may be set, for example, at about 0.1 to 10 fold (weight ratio), preferably at about 0.2 to 2 fold (weight ratio), to the dose of 2-iminopyrrolidine derivative.

When the 2-iminopyrrolidine derivative is combined with clopidogrel, doses of these compounds are not particularly limited. For example, the 2-iminopyrrolidine derivative may be administered to an adult (body weight: 60 kg) at a daily dose of 1 mg to 1,000 mg, preferably 10 mg to 600 mg, more preferably 50 mg to 400 mg; and clopidogrel may be administered to an adult (body weight: 60 kg) at a daily dose of 10 mg to 1,000 mg, preferably 50 mg to 600 mg, more preferably 75 mg to 300 mg. Further, the ratio of the dose of clopidogrel may be set, for example, at about 0.1 to 10 fold (weight ratio), preferably at about 0.2 to 2 fold (weight ratio), to the dose of 2-iminopyrrolidine derivative.

At the time of initial administration, it is also possible to administer one or both of the 2-iminopyrrolidine derivative and the compound (B) at a higher dose(s) than the maintenance dose(s) in order to allow the maximum efficacy of the drug(s) to be manifested promptly.

In the present invention, it is possible to treat or ameliorate at least one disease selected from the group consisting of acute coronary syndrome (for example, ST-segment non-elevation myocardial infarction and unstable angina), atherothrombosis (for example, peripheral arterial occlusive disease), restenosis, hypertension, stable angina, exercise-induced angina, angina at rest, arrhythmia, cardiac failure, ST-segment elevation myocardial infarction, thrombotic stroke, thromboembolic stroke, venous thromboembolism, deep venous thrombosis, pulmonary embolism, atherosclerosis, peripheral vascular disease, inflammatory disease, cerebral ischemia, cerebral infarction, other occlusive vascular diseases, disseminated intravascular coagulation, rheumatism, asthma, glomerulonephritis, osteoporosis, neurological disorders, etc., by combined use of at least one specific 2-iminopyrrolidine derivative and at least one other compound (B). Preferably, the disease to be treated or ameliorated by the present invention is a heart disease. The heart disease which can be treated or ameliorated by the present invention is, for example, at least one disease selected from the group consisting of acute coronary syndrome, atherothrombosis, restenosis, hypertension, stable angina, arrhythmia, cardiac failure, ST-segment elevation myocardial infarction and cerebral infarction.

In the present invention, when the above-described 2-iminopyrrolidine derivative and the other compound (B) are used in combination, those diseases can be treated or ameliorated more effectively than when a compound other than the 2-iminopyrrolidine derivative and the other compound (B) are used in combination.

(5) Method of Treatment and Method of Amelioration

The present invention provides a method of treating or ameliorating heart diseases or the like, comprising administering to a patient an effective amount of at least one (for example, one) specific 2-iminopyrrolidine derivative and an effective amount of at least one other compound (B). In the method of the present invention, the specific 2-iminopyrrolidine derivative is a compound represented by any of the formulas (I) to (VII), etc., preferably a compound represented by the formula (I), etc., and more preferably a hydrobromide of a compound represented by the formula (I). The "compound represented by any of the formulas (I) to (VII), etc." includes pharmacologically acceptable salts of the compound. For the other compound (B), see the description given earlier on combined use of the 2-iminopyrrolidine derivative and the other compound (B). In the method of the present invention, the administration route and the mode of administration of a compound represented by any of the formulas (I) to (VII) and the compound (B) are not particularly limited. See the description given earlier on the administration of the pharmaceutical composition.

(6) Kit

The present invention includes a kit for treating or ameliorating heart diseases or the like, which contains a pharmaceutical composition comprising at least one specific 2-iminopyrrolidine derivative and a pharmaceutical composition comprising at least one other compound (B). In the kit of the present invention, the specific 2-iminopyrrolidine derivative is a compound represented by any of the formulas (I) to (VII), etc., preferably a compound represented by the formula (I), etc., and more preferably a hydrobromide of a compound represented by the formula (I). In the kit of the present invention, for the other compound (B), see the description given earlier on combined use of the 2-iminopyrrolidine derivative and the other compound (B).

The kit may contain, if necessary, accessories and manufacturer's instructions.

(7) Use

The present invention includes use of at least one specific 2-iminopyrrolidine derivative for manufacturing a pharmaceutical composition for treating or ameliorating heart diseases or the like, wherein the pharmaceutical composition is to be used in combination with at least one (for example, one) other compound (B). In the use of the present invention, the specific 2-iminopyrrolidine derivative is a compound represented by any of the formulas (I) to (VII), etc., preferably a compound represented by the formula (I), etc., and more preferably a hydrobromide of a compound represented by the formula (I). In the use of the present invention, for the other compound (B), see the description given earlier on combined use of the 2-iminopyrrolidine derivative and the other compound (B).

Further, the present invention includes at least one compound selected from the formulas (I) to (VII) or a pharmacologically acceptable salt thereof, wherein the compound or the salt is to be used in combination with at least one other compound (B) and to be used for treating or ameliorating heart diseases or the like.

Hereinbelow, the present invention will be described in more detail with reference to the following Examples. However, the present invention is not limited to these Examples.

EXAMPLE 1

(1) Preparation of Hydrobromide of Compound Represented by Formula (I)

1-(3-tert-Butyl-4-methoxy-5-morpholino-phenyl)-2-(5,6-diethoxy-7-fluoro-1-imino-1,3-dihydro-isoindol-2-yl)-ethanone; hydrobromide

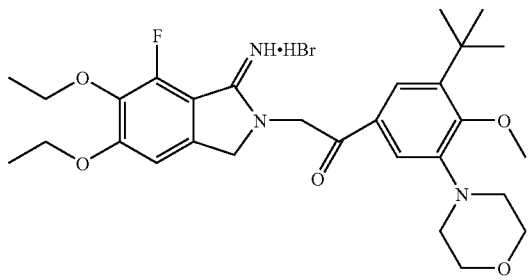

(Step A-1)

1-Bromo-3,4-diethoxy-2-fluorobenzene

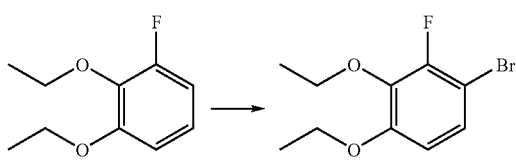

To a solution of 1,2-diethoxy-3-fluorobenzene (150.00 g, 814 mmoL) in acetonitrile (900 mL), a solution of N-bromosuccinimide (NBS) (153.72 g, 864 mmoL) in acetonitrile (1.5 L) was added dropwise under ice cooling and stirred overnight at room temperature. After evaporation of the solvent, ethyl acetate was added to the residue, followed by washing with water. The resultant aqueous layer was re-extracted with ethyl acetate, and the extract was mixed with the previously obtained organic layer. The organic layer was washed with water, saturated saline and water in this order and then dried over anhydrous magnesium sulfate. The resultant solution was concentrated to obtain an oily material. Hexane was added to the oily material, and the crystals deposited were removed by filtration. The solution was re-concentrated to obtain an oily material, which was distilled under reduced pressure to give 205.65 g of the captioned compound (yield: 96%).

b. p ° C.: 110-111° C./2 mmHg $^1$H-NMR (CDCl$_3$) δ:1.35 (3H, t, J=6.8 Hz), 1.42 (3H, t, J=6.8 Hz), 4.03 (2H, q, J=6.8 Hz), 4.11 (2H, q, J=6.8 Hz), 6.57 (1H, dd, J=2.0, 9.3 Hz), 7.15 (1H, dd, J=7.3, 8.8 Hz).

MS m/z: 262 (M$^+$)

(Step A-2)

3,4-Diethoxy-2-fluorobenzonitrile

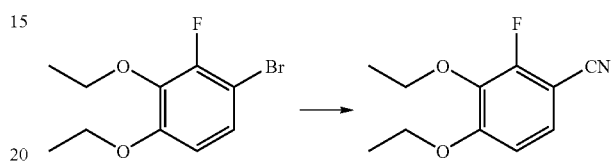

To a solution of 1-bromo-3,4-diethoxy-2-fluorobenzene (12.0 g, 45.6 mmoL) in N,N-dimethylformamide (DMF) (60 mL), copper (I) cyanide (6.8 g, 68.3 mmoL) was added at room temperature and then stirred at 155° C. for 3 hours. After ice cooling the reaction solution, ethyl acetate and 28% aqueous ammonium were added thereto to separate the organic layer. This organic layer was washed with water and saturated saline and dried over anhydrous magnesium sulfate. After filtration, the solvent was evaporated. The residue was purified by silica gel column chromatography (n-hexane, ethyl acetate) to give 9.0 g of the captioned compound (yield: 94.3%).

$^1$H-NMR (CDCl$_3$) δ:1.35 (3H, t, J=6.8 Hz), 1.49 (3H, t, J=6.8 Hz), 4.14 (2H, q, J=6.8 Hz), 4.15 (2H, q, J=6.8 Hz), 6.70 (1H, dd, J=1.5, 8.8 Hz), 7.24 (1H, dd, J=6.4, 8.8 Hz).

MS m/z: 209 (M$^+$)

(Step A-3)

3,4-Diethoxy-2-fluoro-6-formylbenzonitrile

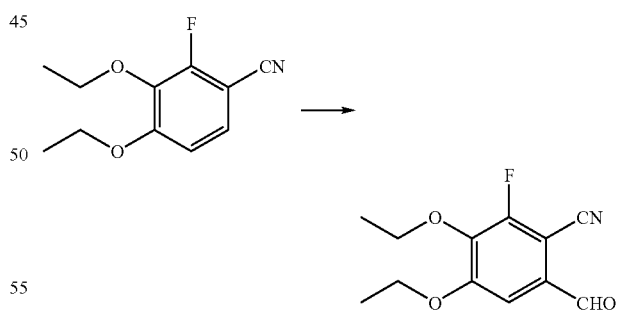

To a reaction vessel, THF (18.7 kg) was added under nitrogen gas flow, followed by addition of n-heptane (13.7 kg) and 2,2,6,6-tetramethylpiperidine (TMP) (7.50 kg, 53.1 mol). The resultant mixture was stirred. The reaction system was closed, and the reaction mixture was cooled to −15° C. under nitrogen slightly positive pressure and stirred overnight. A solution of 15% n-butyllithium-hexane (22.4 kg, 50.2 mol) whose inside temperature was set at −42.3° C. was added dropwise at the inside temperature of −10° C. or below. The inside of the dripping tube was rinsed with n-heptane (0.68 kg). Subsequently, the inside temperature was decreased to −86.9° C., followed by dropwise addition of a solution of 3,4-diethoxy-2-fluorobenzonitrile (7.00 kg, 33.5 mol) in THF (10.68 kg). The dripping tube was rinsed with THF (1.8 kg). About 1 hour later, a solution of N,N-dimethylformamide (4.89 kg, 66.9 mol) in THF (4.49 kg) was added dropwise. Thirty-three minutes after completion of the addition of the DMF-THF solution, n-heptane (34.5 kg) was added dropwise. After stirring for 1 hour, a solution of acetic acid (10.5 kg, 175.0 mol) in THF (2.99 kg) was added to make the temperature of the external bath 10° C. Fifty-five minutes later, water (50.4 L) was added dropwise, followed by addition of n-heptane (17.2 kg). The temperature of the external bath was made 10° C., followed by stirring for 14.7 hr. The reaction solution was pulled out and divided into halves, which were centrifuged separately. The resultant crystals from one half were washed with n-heptane (5 L), water (5 L) and n-heptane (5 L) to give 4.85 kg of crude product, which were stored in a refrigerator. The other half (slurry) was treated in the same manner to give 5.25 kg of crude product (total of the wet product: 10.10 kg).

The wet product was placed in a reaction vessel, to which water (40 L) and n-heptane (80 L) were added and stirred at 25° C. for 18.7 hours. The reaction solution was pulled out, and the wall of the reaction vessel was rinsed with a mixture of n-heptane (5 L) and water (10 L). The reaction solution and the rinsing solution were mixed and subjected to centrifugation. The resultant crystals were washed with n-heptane (5 L), water (5 L) and n-heptane (5 L) to give 10.30 kg of the captioned compound as a wet product.

The wet product was placed in a conical drier and dried under reduced pressure at 50° C. for 20 hr and at 55° C. for 4 hr to give 5.98 kg of the captioned compound as slightly greenish white powder-like crystals (yield: 75.3%).

$^1$H-NMR (CDCl$_3$) δ:1.39 (3H, t, J=6.8 Hz), 1.49 (3H, t, J=6.8 Hz), 4.20 (2H, q J=6.8 Hz), 4.28 (2H, q, J=6.8 Hz), 7.32 (1H, d, J=1.5 Hz), 10.19 (1H, s)

MS m/z: 238 [(M+H)$^+$]

(Step A-4)

3,4-Diethoxy-2-fluoro-6-hydroxymethylbenzonitrile

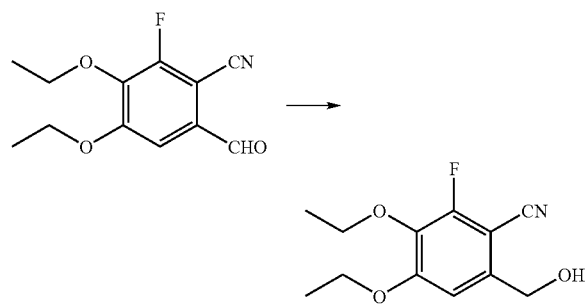

To a reaction vessel, 3,4-diethoxy-2-fluoro-6-formylbenzonitrile (5.90 kg, 24.87 mol) and ethyl acetate (59.0 L) were added under a nitrogen atmosphere, followed by addition of sodium triacetoxyborohydride (NaB(OAc)$_3$H) (11.70 kg) while stirring. After stirring for 30 min, the inside temperature was raised to 40° C., and the reaction solution was stirred for 2 hours. Then, the reaction solution was cooled. Water (2 L) was added thereto slowly and dropwise at the inside temperature of 15° C. to thereby decompose excessive sodium triacetoxyborohydride. Water (27.5 L) was further added thereto. The temperature of the external bath was raised to 40° C. to dissolve insoluble matter, followed by re-cooling and separation of liquid layers. The resultant organic layer was washed with aqueous sodium bicarbonate solution twice and then with saline. The thus obtained organic layer was cooled with the external bath temperature of 10° C. and left overnight.

The temperature of the external bath was raised to 50° C., and the organic layer was concentrated to 14 L under reduced pressure. Then, the temperature of the external bath was lowered to 10° C., and n-heptane (59 L) was added to the organic layer and stirred for 2.8 hr. The deposited crystals were filtered and washed with n-heptane (5.9 L) to give 5.66 kg of the captioned compound as a wet product. This wet product was placed in a conical drier and dried under reduced pressure at 50° C. for 18.3 hr to give 5.17 kg of the captioned compound as slightly yellowish white powder-like crystals (yield: 87%).

$^1$H-NMR (CDCl$_3$) δ:1.36 (3H, t, J=6.8 Hz), 1.48 (3H, t, J=6.8 Hz), 4.12 (2H, q, J=6.8 Hz), 4.17 (2H, q, J=6.8 Hz), 4.82 (2H, s), 5.53 (1H, s), 6.95 (1H, s).

MS m/z: 240 (M+H)$^+$ (Step A-5)

Methanesulfonic acid
2-cyano-4,5-diethoxy-3-fluorobenzyl

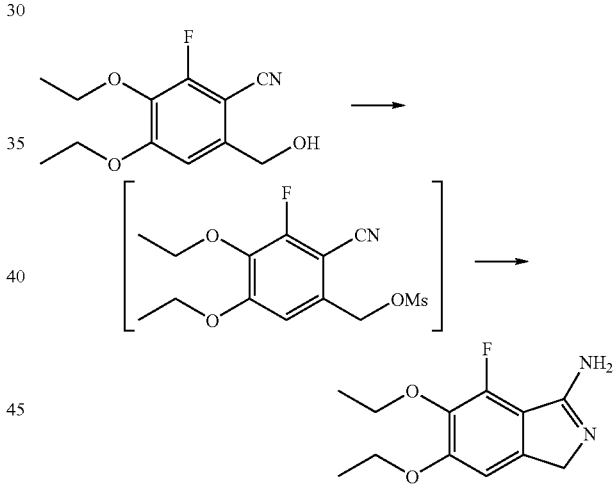

To a reaction vessel, 3,4-diethoxy-2-fluoro-6-(hydroxymethyl)benzonitrile (4.50 kg, 18.81 mol) and 1,2-dimethoxyethane (45 L) were added and stirred. The reaction solution was cooled, and the inside of the reaction system was placed under a nitrogen atmosphere. Triethylamine (2.47 kg, 24.45 mol) was added at the inside temperature of 8.4° C. Further, methanesulfonyl chloride (2.59 kg, 22.61 mol) was added dropwise in such a manner that the inside temperature did not exceed 20° C. After stirring for 34 min, the inside of the reaction system was placed under nitrogen gas flow, and the cooling was stopped. To the reaction solution, toluene (45 L) and 0.5 N hydrochloric acid (9 L) were added to separate liquid layers. The resultant organic layer was washed with water (18 L), aqueous solution of 10% sodium hydrogencarbonate (18 L), 10% saline (18 L) and water (18 L), and concentrated under reduced pressure. After addition of toluene (45 L) to the thus concentrated solution, the solution was re-concentrated under reduced pressure. After cooling the thus concentrated solution, it was diluted with toluene (40 L). The resultant dilution was withdrawn into two containers in equal volumes. The wall of the reaction vessel was rinsed with toluene (5 L). This rinsing solution was divided into halves, which were mixed with the halves of the above dilution, respectively. Thus, two portions of a solution of methanesulfonic acid 2-cyano-4,5-diethoxy-3-fluorobenzyl in toluene were obtained. These portions were designated solution A and solution B. After determination of the weights of these solutions (solution A: 32.16 kg, solution B: 32.24 kg), aliquots of these solutions were taken as samples and subjected to HPLC for quantitative determination. Toluene solution of methanesulfonic acid 2-cyano-4,5-diethoxy-3-fluorobenzyl in toluene Property: brown toluene solution, Quantitatively determined value: 5.79 kg (solution A: 2.92 kg and solution B: 2.87 kg)

Yield: 96.9%, HPLC purity: solution A: 98.8% and solution B: 98.6%

$^1$H-NMR (400 MHz, CDCl$_3$) δ:1.38 (3H, t, J=6.8 Hz), 1.50 (3H, t, J=6.8 Hz), 3.13 (3H, s), 4.17 (4H, q, J=6.8 Hz), 5.28 (2H, s), 6.89 (1H, d, J=1.0 Hz).

MS m/z: 317 (M$^+$)

(Step A-6)

5,6-Diethoxy-7-fluoro-3H-isoindol-1-ylamine

To a reaction vessel, the toluene solution A of methanesulfonic acid 2-cyano-4,5-diethoxy-3-fluorobenzyl obtained in the preceding step [32.16 kg (2.92 kg as methanesulfonic acid 2-cyano-4,5-diethoxy-3-fluorobenzyl), 9.20 mol] and toluene (170 L) were added and stirred at room temperature. The reaction solution was cooled to 20° C. or below. After stirring was stopped, the inside of the reaction system was replaced with ammonia. After stirring, ammonia was re-charged up to 0.86 MPa. The reaction solution was continuously stirred overnight. Subsequently, ammonia gas was leaked. To the reaction solution, water (35 L) and then 2 N hydrochloric acid (35 L) were added to separate liquid layers. To the resultant organic layer, 1 N hydrochloric acid (23.4 L) was added to separate liquid layers. The resultant aqueous layer was mixed with the previously obtained aqueous layer and subjected to clarifying filtration. After rinsing with water (10 L), the filtrate was transferred into a reaction vessel, which was washed with water (15 L) to cool the reaction solution. Aqueous solution of 5 N sodium hydroxide (7.18 L) was added thereto dropwise. The reaction solution was heated with the external bath at 30° C. and stirred for about 4 hr. The resultant reaction solution was cooled and, at its temperature of 17.4° C., aqueous solution of 5 N sodium hydroxide (12.82 L) was added thereto dropwise and stirred overnight. The deposited crystals were filtered and washed with water (30 L) and tert-butyl methyl ether (6 L) to give 2.29 kg of a wet product. This wet product was dried in a conical dryer at 40° C. under reduced pressure to give the captioned compound (1.85 kg) as slightly yellowish white powder-like crystals.

Property: slightly yellowish white powder-like crystals, Yield amount: 1.85 kg, Yield: 84%, HPLC purity: 97.5%, Moisture content: 0.22%

$^1$H-NMR (400 MHz, DMSO-d$_6$) δ:1.24 (3H, t, J=7.0 Hz), 1.34 (3H, t, J=7.0 Hz), 4.01 (2H, q, J=7.0 Hz), 4.17 (2H, q, J=7.0 Hz), 4.38 (2H, s), 6.04 (2H, bs), 7.04 (1H, s).

MS m/z: 239 (M+H)$^+$ (Step B-1)

1-(3-tert-Butyl-4-hydroxyphenyl)ethanone

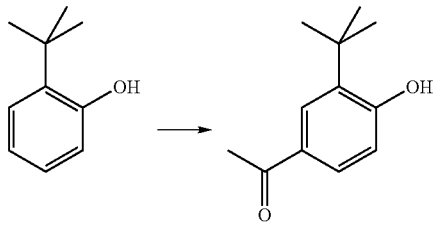

Aluminium chloride (44.4 g, 333 mmol) was cooled to −45° C., followed by addition of toluene (1.25 L). 2-tert-butylphenol (50.0 g, 333 mmol) was added further and stirred for 2 hours. Further, acetyl chloride (26.1 g, 333 mmol) was added dropwise and stirred for 2.5 hours. The resultant reaction solution was added to ice-cooled water (250 mL) dropwise and stirred at room temperature. Crystals were collected by filtration and dried under reduced pressure (50° C.) to give 48.7 g of the captioned compound as white crystals (yield: 76.1%; HPLC purity: 99.8%).

$^1$H-NMR (400 MHz, CDCl$_3$) δ:1.43 (9H, s), 2.57 (3H, s), 6.17 (1H, s), 6.76 (1H, d, J=8.0 Hz), 7.73 (1H, dd, J=2.4, 8.0 Hz), 7.96 (1H, d, J=2.4 Hz).

MS m/z: 193 [(M+H)+]

(Step B-2)

1-(5-Bromo-3-tert-butyl-4-hydroxyphenyl)ethanone

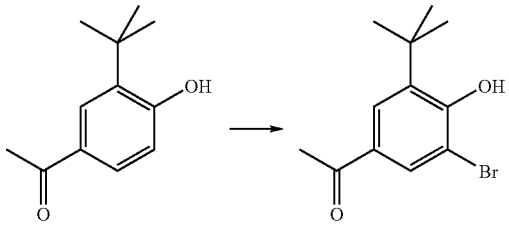

1-(3-tert-Butyl-4-hydroxyphenyl)ethanone (690.9 g, 3.75 mol) was dissolved in acetonitrile (6.05 L). While stirring under ice-cooling, a solution of N-bromosuccinimide (701.28 g, 3.94 mol) in acetonitrile (5 L) was added thereto dropwise. The temperature of the resultant mixture was raised to room temperature, and then the solvent was concentrated to about 3 L. n-Heptane (5 L) and water (5 L) were added thereto for extraction and liquid separation. The aqueous layer was further extracted with n-heptane (2 L) and separated into layers. The organic layer was mixed with the previously obtained organic layer, washed with aqueous solution of 5% sodium thiosulfate (1 L) and water (2 L), and concentrated under reduced pressure (35° C.) to give 977.0 g of the captioned compound as a slightly brown oily material (yield: 99.1%; HPLC purity: 95.8%).

$^1$H-NMR (400 MHz, CDCl$_3$) δ:1.42 (9H, s), 2.55 (3H, s), 6.26 (1H, s), 7.88 (1H, d, J=2.0 Hz), 7.99 (1H, d, J=2.0 Hz).

MS m/z: 271 [(M+H)+]

(Step B-3)

2-Bromo-6-tert-butyl-4-(1,1-dimethoxyethyl)anisole

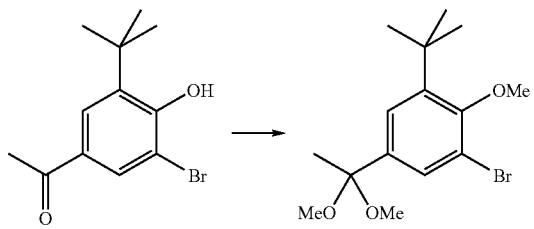 [SMILES: CC(=O)c1cc(Br)c(O)c(C(C)(C)C)c1 ; COc1c(Br)cc(C(C)(OC)OC)cc1C(C)(C)C]

To 1-(5-bromo-3-tert-butyl-4-hydroxyphenyl)ethanone (678 g, 2.50 mol), methanol (678 mL), trimethyl orthoformate (796 g, 7.50 mol) and (±)-10-camphorsulfonic acid [(±)-CSA] (11.6 g, 0.050 mol, 2 mol %) were added and stirred under a nitrogen atmosphere. Alter stirring for 2.7 hours, N,N-dimethylformamide (1.7 L) were added thereto. The resultant mixture was cooled on ice. Subsequently, methyl iodide (700 g) and potassium carbonate (518 g) were added in this order and stirred at room temperature. After stirring for 5.5 hours, water (4750 mL) and n-heptane (4750 mL) were added to the reaction solution to separate liquid layers. The organic layer was washed with water (2370 mL), and sodium sulfate (120.2 g) was added thereto and stirred. Then, this layer was vacuum filtered. At this time, washing with n-heptane (250 mL) was carried out. The solvent in the filtrate was evaporated (50° C.) to give 808 g of the captioned compound as a brown oily material (yield: 98%; HPLC purity: 96.8%).

$^1$H-NMR (400 MHz, DMSO-$d_6$) δ:1.35 (9H, s), 1.43 (3H, s), 3.07 (6H, s), 3.86 (3H, s), 7.32 (1H, d, J=2.0 Hz), 7.47 (1H, d, J=2.0 Hz).

MS m/z: 330 (M+)

(Step B-4)

4-[3-tert-Butyl-5-(1,1-dimethoxyethyl)-2-methoxyphenyl]morpholine

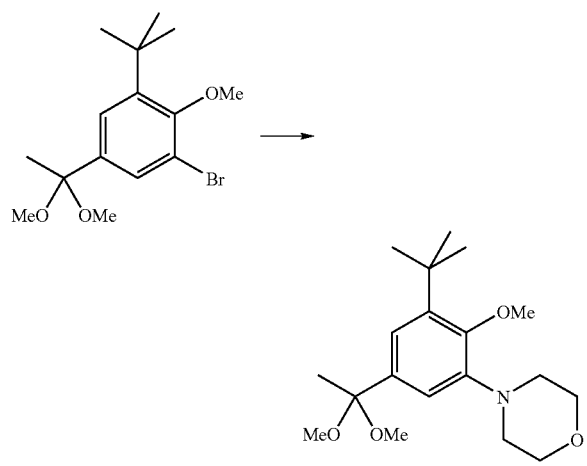

Under a nitrogen atmosphere, 2-bromo-6-tert-butyl-4-(1,1-dimethoxyethyl)anisole (650 g, 1.962 mol), palladium acetate (4.4 g 19.6 mmol, 1 mol %) and (±)-BINAP (18.3 g, 29.4 mmol, 1.5 mol %) were dissolved in 1,2-dimethoxyethane (1.96 L) at room temperature. To the resultant solution, morpholine (205 g, 2.36 mol) and sodium tert-butoxide (264 g, 2.75 mol) were added.

After stirring at 85° C. for 2 hours, the temperature of the reaction solution was lowered to 30° C. or below while stirring under ice-cooling. Insoluble matter was filtered, and the filtration residue was washed with 1,2-dimethoxyethane (1 L). After the solvent was evaporated under reduced pressure, methanol (600 mL), N,N-dimethylformamide (1.2 L) and n-heptane (6 L) were added for extraction and liquid layer separation. Further, the N,N-dimethylformamide layer was extracted twice with n-heptane (3 L) and liquid layers were separated. Then, the resultant n-heptane layers were mixed and washed with methanol (200 mL) and water (1.8 L). To the resultant n-heptane layer, thiocyanuric acid (TMT) (13 g) was added and stirred for 15 hours at room temperature. Then, the resultant mixture was filtered through Celite. The filtration residue was washed with n-heptane (500 mL). The filtrate was washed with aqueous solution of 87% N,N-dimethylformamide (1.3 L) and water (1.3 L) and then concentrated under reduced pressure (50° C.) to give 618 g of the captioned compound as a brown oily material (yield: 93.3%, HPLC purity: 99.5%).

$^1$H-NMR (400 MHz, CDCl$_3$) δ:1.37 (9H, s), 1.52 (3H, s), 3.07 (4H, t, J=4.4 Hz), 3.18 (6H, s), 3.88 (4H, t, J=4.4 Hz), 3.94 (3H, s), 6.97 (1H, d, J=2.4 Hz), 7.10 (1H, d, J=2.4 Hz).

MS m/z: 337 (M+)

(Step B-5)

2-Bromo-1-(3-tert-butyl-4-methoxy-5-morpholinophenyl)ethanone

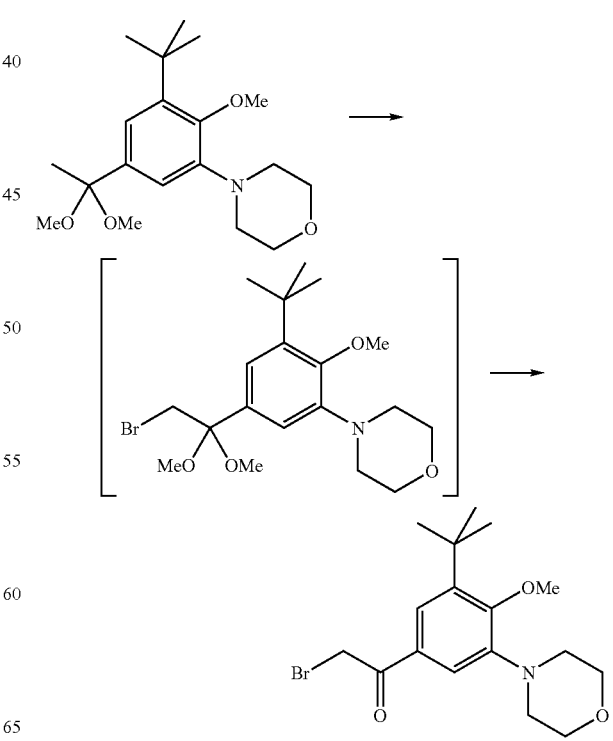

4-[5-(1,1-Dimethoxyethyl)-3-tert-butyl-2-methoxyphenyl]morpholine (600 g, 1.78 mol) was dissolved in a mixed solvent of tetrahydrofuran (2.67 L) and methanol (0.89 L). To this solution, phenyltrimethylammonium tribromide (716 g, 1.87 mol) was added at 7° C. under a nitrogen atmosphere. After stirring for 1 hour, aqueous solution of 5% sodium thiosulfate (660 mL) was added to the reaction solution. Further, water (4.68 L) was added thereto and stirred for 1 hour. Then, crystals were collected by filtration to give crude crystals of the captioned compound as yellowish flesh colored crystals.

The crude crystals of the captioned compound were suspended and stirred in a mixed solvent of n-heptane (1980 mL) and 2-propanol (660 mL) at 7° C. After stirring for 13 hours, the crystals were collected by filtration and washed with 10% 2-propanol/n-heptane solution (660 mL) and n-heptane (660 mL). Then, the crystals were dried under reduced pressure (50° C.) to give 566.2 g of the captioned compound light yellowish white crystals (yield: 86.0%, HPLC purity: 99.0%).

4-[5-(2-Bromo-1,1-dimethoxyethyl)-3-tert-butyl-2-methoxyphenyl]morpholine $^1$H-NMR (400 MHz, CDCl$_3$) δ:1.37 (9H, s), 3.07 (4H, t, J=4.4 Hz), 3.24 (6H, s), 3.57 (2H, s), 3.88 (4H, t, J=4.4 Hz), 3.94 (3H, s), 6.98 (1H, d, J=2.4 Hz), 7.08 (1H, d, J=2.4 Hz).

2-Bromo-1-(3-tert-butyl-4-methoxy-5-morpholinophenyl)ethanone $^1$H-NMR (400 MHz, CDCl$_3$) δ: 1.40 (9H, s), 3.09 (4H, t, J=4.4 Hz), 3.90 (4H, t, J=4.4 Hz), 3.99 (3H, s), 4.41 (2H, s), 7.52 (1H, d, J=2.0 Hz), 7.69 (1H, d, J=2.0 Hz).

MS m/z: 369 (M+)

(Step B-6: Final Step)

1-(3-tert-Butyl-4-methoxy-5-morpholinophenyl)-2-(5,6-diethoxy-7-fluoro-1-imino-1,3-dihydro-2H-isoindol-2-yl)ethanone hydrobromide

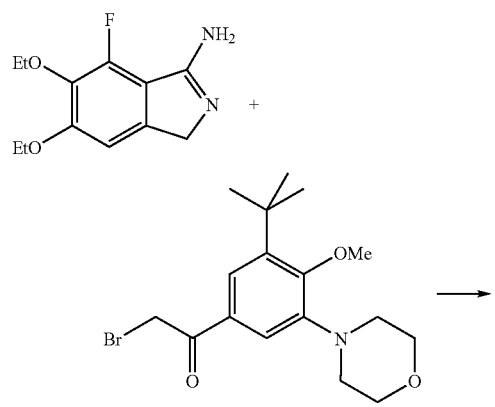

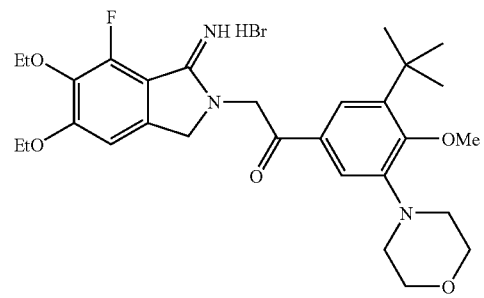

2-Bromo-1-(3-tert-butyl-4-methoxy-5-morpholinophenyl)ethanone (550 g, 1.485 mol) was dissolved in tetrahydrofuran (3 L) and subjected to clarifying filtration. A solution of 5,6-diethoxy-7-fluoro-3H-isoindol-1-ylamine (300 g, 1.254 mol) in tetrahydrofuran (4.5 L) was added dropwise to the above solution in 3 portions (100 g/1.5 L×3 times) while stirring at the ambient temperature of 6° C. After completion of the dripping, crystals were deposited. After stirring for 18 hours, the deposited crystals were collected by filtration and washed with ice-cooled tetrahydrofuran (1.2 L) to give 696.5 g of the captioned compound as wet crystals.

These wet crystals (693.5 g) were dissolved in 50% tetrahydrofuran/water (5 L) at 50° C. This solution was subjected to clarifying filtration and then washed with 50% tetrahydrofuran/water (0.5 L). While stirring under ice-cooling, water (2.5 L) was added to the filtrate. After addition of seed crystals (1.52 g), water (7.5 L) was added dropwise. After stirring at 8° C. for 15 hours, crystals were collected by filtration, washed with water (2 L) and air-dried for 26 hours (60° C.). Thus, 622.1 g of the captioned compound was obtained as white crystals (yield: 81.5%, HPLC purity: 99.6%).

(Step B-6, Alternative Method (1): Final Step)

5,6-Diethoxy-4-fluoro-1H-3-isoindolamine (20 g) and 2-bromo-1-[3-(tert-butyl)-4-methoxy-5-morpholinophenyl]-1-ethanone (34.2 g) were dissolved in dimethylformamide (300 ml) and stirred at room temperature for 48 hours. After the solvent was evaporated under reduced pressure, ethyl acetate (500 mL) was added to the residue for crystallization. The resultant crystals were filtered and washed with ethyl acetate to give the compound of interest (40 g) as white crystals.

$^1$H-NMR (DMSO-d$_6$) δ (ppm) 1.29 (3H, t, J=6.8 Hz) 1.36 (9H, s) 1.39 (3H, t, J=6.8 Hz)) 2.95-3.12 (4H, m) 3.75-3.84 (4H, m) 3.94 (3H, s) 4.12 (2H, q) 4.20 (2H, q, J=6.8 Hz) 4.78 (2H, s) 5.46 (2H, s) 7.33 (1H, s) 7.49 (1H, s) 7.59 (1H, s)

MS: m/e (ESI) 528.2 (MH+)

(Step B-6, Alternative Method (2): Final Step)

1-(3-tert-butyl-4-methoxy-5-morpholino-phenyl)-2-(5,6-diethoxy-7-fluoro-1-imino-1,3-dihydro-isoindol-2-yl)-ethanone; hydrochloride

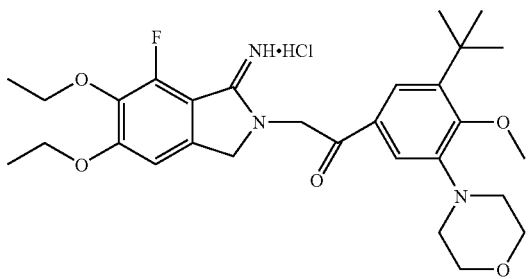

5,6-Diethoxy-4-fluoro-1H-3-isoindolamine (3.2 g) and 2-bromo-1-[3-(tert-butyl)-4-methoxy-5-morpholinophenyl]-1-ethanone (4.8 g) were dissolved in dimethylformamide (15 mL) and stirred at room temperature for 48 hours. After the solvent was evaporated under reduced pressure, ethyl acetate (50 mL) was added to the residue for crystallization. The resultant crystals were collected by filtration and then washed with ethyl acetate to give the compound of interest (2.56 g) as white crystals.

$^1$H-NMR (DMSO-d$_6$) δ (ppm) 1.29 (3H, t, J=6.8 Hz) 1.36 (9H, s) 1.39 (3H, t, J=6.8 Hz)) 2.95-3.04 (4H, m) 3.77-3.85 (4H, m) 3.94 (3H, s) 4.11 (2H, q) 4.20 (2H, q, J=6.8 Hz) 4.77 (2H, s) 5.46 (2H, s) 7.32 (1H, s) 7.49 (1H, s) 7.59 (1H, s)

EXAMPLE 2

The activities of the compounds represented by the formulas (I) to (VII) or the like may be determined by the procedures described below.

(1) Procedures for In Vitro Tests on the Compounds of the Formulas (I) to (VII) or the Like (a) Preparation of Platelet Membranes Blood samples are collected from healthy persons who have not taken any medicine during the last one week, and 3.8% citric acid (at a citric acid:blood ratio of 1:9) is added as an anticoagulant. The resultant mixture is then centrifuged for 10 minutes at 100 g at room temperature to yield platelet rich plasma (PRP). The platelet precipitate obtained by centrifuging the PRP is suspended in 5 mM Tris-HCl/5 mM EDTA (pH 7.5), homogenized in a Dounce homogenizer and then centrifuged for 60 minutes at 40000 g to yield platelet membranes. The resultant platelet membranes are suspended in a solution prepared by adding DMSO (dimethyl sulfoxide) to Buffer 1 [a 50 mM Tris-HCl buffer (pH 7.5) containing 10 mM MgCl$_2$ and 1 mM EGTA (ethylene glycol tetraaeetic acid)] to give a concentration of 1%, and stored at −80° C.

(b) Thrombin Receptor Radioligand Binding Assay

Thrombin receptor antagonist activity is evaluated using a modification of Ahn et al.'s method of thrombin receptor radioligand binding assay (Ahn et al., Mol. Pharmacol., Vol. 51, pp. 350-356 (1997)). A solution for preparing test compound solutions is obtained by adding to Buffer 1 [50 mM Tris-HCl buffer (pH 7.5), 10 mM MgCl$_2$ and 1 mM EGTA] bovine albumin and DMSO to give concentrations of 0.1% and 20%, respectively. Variously diluted test compound solutions prepared with the above solution are added to 96-well Multiscreen plates (20 µl/well). Subsequently, 80 µl of [$^3$H] Ala-(4-fluoro)Phe-Arg-(cyclohexyl)Ala-(homo)Arg-Tyr-NH$_2$ (high affinity TRAP) which has been diluted to 25 nM with Buffer 1 is added. Further, 100 µl of a platelet membrane solution (0.4 mg/mL) prepared in advance is added and mixed. Then, the plates are incubated at 37° C. for 1 hour. Following vacuum filtration of the reaction solution, the plates are washed three times with 200 µl of Buffer 1. Subsequently, 30 µl of liquid scintillator is added thereto to determine the radioactivity of each plate with a Packard Top Counter. Binding ratio is determined as follows: the value obtained by subtracting non-specific binding from the radioactivity in the presence of test compound is divided by specific binding (which is obtained by subtracting non-specific binding from the binding in the absence of test compound). From the resultant binding ratio, IC$_{50}$ is calculated. It should be noted here that the specific binding is the value obtained when 10 µM high affinity TRAP has been added.

(2) Cynomolgous Ex Vivo Platelet Aggregation (a) Drug Administration and Blood Sampling At least one compound selected from the group consisting of the formulas (I) to (VII) or a pharmacologically acceptable salt thereof and at least one other compound (B) selected from group B described earlier are administered orally, single or in mixture, to cynomolgous (*Macaca fascicularis*) in a state of arousal. When at least one other compound selected from group B is continuously infused intravenously, inhalation anesthesia is carried out using an anesthetic gas (composition: nitrous oxide 2 L/min, oxygen 1 L/min, isoflurane 0.5%), following induction of anesthesia using ketamine. A catheter for feeding a test substance is inserted into the brachial vein using an indwelling needle. A drug is fed into the vein for a specific time period (for example, 90 min) using an infusion pump. Blood samples are collected before oral administration of test substance(s) and after completion of the administration of both test substances. Blood samples are collected in an amount of 1.8 mL/sample from the brachial vein or saphenous vein using a syringe containing 200 µl of 3.8% citric acid solution as an anticoagulant.

(b) PRP Aggregation

The collected blood samples are transferred into Eppendorf tubes and centrifuged at room temperature at 6400 rpm for 5 seconds, followed by isolation of the supernatant as PRP. The PRP-isolated blood is centrifuged further at 10,000 rpm for 5 minutes to isolate platelet poor plasma (PPP). The PRP is diluted with the PPP to give a platelet concentration of 3×10$^5$/µl. PRP aggregation is measured according to Born et al.'s turbidity method. PRP (225 µl) is placed in a measurement channel and heated to 37° C. Thrombin receptor activating peptide (TRAP; 25 µl) is added thereto. Aggregation curve based on turbidity change is recorded for 6 minutes. The area below this aggregation curve is evaluated as aggregation intensity.

(3) Procedures for In Vitro Platelet Aggregation

Blood samples are collected from healthy persons who have not taken any medicine during the last one week, and 3.8% citric acid (at a citric acid:blood ratio of 1:9) is added as an anticoagulant. The resultant mixture is then centrifuged for 10 minutes at 100 g at room temperature to isolate PRP The PRP-isolated blood is centrifuged further for 5 minutes at 1000 g to isolate PPP. Platelet count is determined with an automated multi-item hematology analyzer (K4500; Sysmex); PRP is diluted with PPP to give a platelet concentration of approximately 300,000/µl. Variously diluted solutions of the compounds selected from the group consisting of the formulas (I) to (VII) and PRP are preincubated at 37° C. for 60 minutes. To the preincubated PRP (175 µl), solutions of compound (B) of various concentrations (25 µl each) are added.

As a fibrin polymerization inhibitor, GPRP-NH$_2$ (final concentration: 1 mM) (25 µl) is further added. Platelet aggregation capacity is measured with an aggregometer (MC Medical). After the above mixture is kept at 37° C. for 3 minutes, 25 µl of thrombin solution (1 U/mL) is added thereto and aggregation for 6 minutes is examined. By comparing the areas below aggregation curves, inhibitory effects are evaluated. When an aggregation initiator other than thrombin is used, GPRP-NH$_2$ is not added and the volume of PRP is changed to 200 µl.

EXAMPLE 3

Example 3-1

At least one compound selected from the group consisting of the formulas (I) to (VII) or a pharmacologically acceptable salt thereof and at least one other compound (B) selected from group B are administered orally, single or in mixture, to male Hartley guinea pigs. As a vehicle, 0.5% methylcellulose solution or an aqueous solution containing dimethylsulfoxide and Tween 20 is used. (These compounds may be administered repeatedly.)

At a specific time after the oral administration, guinea pigs are anesthetized by intraperitoneal administration of sodium pentobarbital. Under anesthesia, the cervical vein is exposed and a polyethylene tube is cannulated thereinto for administering rose bengal. The femoral artery is exposed and fitted with a probe for blood flow measurement. A site upstream of the probe is irradiated with green light (wavelength 540 nm, 500,000 lux). Five minutes after the irradiation, a rose bengal solution dissolved in physiological saline to give a concentration of 5 mg/mL is administered over about 1 minute (5 mg/kg). Time to complete cessation of blood flow is measured.

From these experimental data, antithrombotic effects from individual compounds and from combined use of them are evaluated.

Example 3-2

A hydrobromide of a compound represented by the formula (I) (hereinafter, referred to as "the compound of Example 1") and aspirin were dissolved with DMSO to give concentrations of 200 mg/mL and 1000 mg/mL, respectively. Using the resultant DMSO solutions, Tween 20 and distilled water, the following 4 types of aqueous solutions were prepared in such a manner that the concentrations of DMSO and Tween 20 become 5% and 2%, respectively: 1) vehicle without test compounds; 2) the compound of Example 1 alone (6 mg/mL); 3) solution of aspirin alone (50 mg/mL) and 4) mixed solution composed of the compound of Example 1 (6 mg/mL) and aspirin (20 mg/mL). The thus prepared solution was administered to male Hartley guinea pigs orally at a dose of 5 mL/kg. About 80 minutes after the administration, guinea pigs were anesthetized by intraperitoneal administration of sodium pentobarbital. Under anesthesia, the cervical vein was exposed and a polyethylene tube was cannulated thereinto for administering rose bengal. The femoral artery was exposed and fitted with a probe for blood flow measurement. About 115 minutes after the compound administration, a site upstream of the probe was irradiated with green light (wavelength 540 nm, 500,000 lux). Five minutes after the irradiation, a rose bengal solution dissolved in physiological saline to give a concentration of 5 mg/mL was administered over about 1 minute (5 mg/kg). Blood flow time from the beginning of rose bengal administration to the complete cessation of blood flow was measured to evaluate antithrombotic effects.

<Results>

As shown in FIG. 1, while blood flow time in the vehicle-administered control group was 6.72 minutes, administration of the compound of Example 1 (30 mg/kg) and aspirin (100 mg/kg) prolonged blood flow time to 10.77 minutes and 11.30 minutes, respectively. In the group which received combined administration of both drugs, blood flow time was further prolonged to 24.19 minutes.

These results demonstrate that excellent antithrombotic effect can be obtained by combined administration of at least one compound selected from the group of the general formulas (I) to (VII) and a specific compound (B) such as aspirin. Therefore, these results show that it is possible to treat or ameliorate diseases (such as heart diseases) by administering both compounds in combination.

INDUSTRIAL APPLICABILITY

According to the present invention, a pharmaceutical composition comprising at least one 2-iminopyrrolidine derivative and at least one other compound (B) is provided. This pharmaceutical composition is useful in treating or ameliorating diseases, for example, heart diseases.

What is claimed is:

1. A method of treating or ameliorating atherothrombosis, wherein said method comprises: administering to a patient in need thereof an effective amount of a compound of formula (I), or a pharmacologically acceptable salt thereof,

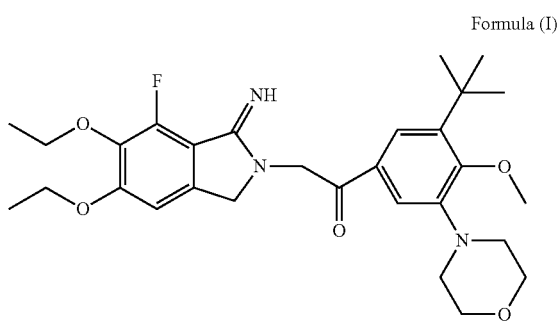 [SMILES: CCOc1cc2c(c(F)c1OCC)C(=N)N(CC(=O)c1cc(N3CCOCC3)c(OC)c(C(C)(C)C)c1)C2]

Formula (I)

and an effective amount of aspirin,
wherein said effective amount of the compound of formula (I) is from about 50 mg to about 400 mg and
wherein said effective amount of aspirin is from about 0.1 to about 10-fold (weight ratio) the effective amount of the compound of formula (I), or its pharmacologically acceptable salt.

2. The method according to claim 1, wherein a hydrobromide salt of the compound of formula (I) is administered.

3. The method according to claim 1, wherein the effective amount of aspirin is about 80 mg to about 350 mg.

* * * * *